(12) United States Patent
Jung et al.

(10) Patent No.: US 12,150,780 B2
(45) Date of Patent: Nov. 26, 2024

(54) ELECTRONIC DEVICE AND METHOD FOR PROVIDING INDIVIDUALIZED GUIDE BASED ON BLOOD PRESSURE RELATED INFORMATION

(71) Applicant: Samsung Electronics Co., Ltd., Suwon-si (KR)

(72) Inventors: Sunok Jung, Suwon-si (KR); Choonghee Ahn, Suwon-si (KR); Hongji Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 331 days.

(21) Appl. No.: 17/692,892

(22) Filed: Mar. 11, 2022

(65) Prior Publication Data

US 2022/0265206 A1   Aug. 25, 2022

Related U.S. Application Data

(63) Continuation of application No. PCT/KR2022/002103, filed on Feb. 11, 2022.

(30) Foreign Application Priority Data

Feb. 24, 2021   (KR) .................. 10-2021-0024509

(51) Int. Cl.
*A61B 5/00* (2006.01)
*A61B 5/021* (2006.01)
*A61B 5/024* (2006.01)

(52) U.S. Cl.
CPC .......... *A61B 5/486* (2013.01); *A61B 5/02108* (2013.01); *A61B 5/02405* (2013.01);
(Continued)

(58) Field of Classification Search
CPC . A61B 5/486; A61B 5/02108; A61B 5/02405; A61B 5/02416; A61B 5/4809;
(Continued)

(56) References Cited

U.S. PATENT DOCUMENTS 8,684,900 B2   4/2014  Tran
2005/0209643 A1   9/2005  Jeruth et al.
(Continued)

FOREIGN PATENT DOCUMENTS

JP      5552853 B2     7/2014
JP   2018-531055 A    10/2018
(Continued)

OTHER PUBLICATIONS

International Search Report dated May 23, 2022, issued in International Application No. PCT/KR2022/002103.
(Continued)

*Primary Examiner* — Jonathan T Kuo
(74) *Attorney, Agent, or Firm* — Jefferson IP Law, LLP

(57) ABSTRACT

An electronic device is provided. The electronic device includes a motion sensor, at least one optical sensor, a processor operatively connected to the motion sensor and the at least one optical sensor, and a memory operatively connected to the processor. The memory may store instructions that cause, when executed, the processor to monitor user state information based on signals received through the motion sensor and the at least one optical sensor, to acquire a sensor value by controlling the at least one optical sensor based on the monitoring, to calculate blood pressure change information according to a user's sleep based on the sensor value, and to provide guide information according to the blood pressure change information.

23 Claims, 8 Drawing Sheets

(52) U.S. Cl.
CPC ........ *A61B 5/02416* (2013.01); *A61B 5/4809* (2013.01); *A61B 5/7275* (2013.01); *A61B 5/7278* (2013.01); *A61B 5/7285* (2013.01); *A61B 5/02438* (2013.01); *A61B 5/7264* (2013.01)

(58) Field of Classification Search
CPC ... A61B 5/7275; A61B 5/7278; A61B 5/7285; A61B 5/02438; A61B 5/7264; A61B 5/00; A61B 5/021; A61B 5/024; A61B 5/11; A61B 5/1118; A61B 2560/0209; A61B 5/0002; A61B 5/1116; A61B 5/1123; A61B 5/681; A61B 5/746; A61B 5/7465

See application file for complete search history.

(56) References Cited

U.S. PATENT DOCUMENTS

| | | |
|---|---|---|
| 2008/0066753 A1 | 3/2008 | Martin et al. |
| 2015/0164351 A1* | 6/2015 | He .................. A61B 5/0285 702/19 |
| 2016/0029964 A1* | 2/2016 | LeBoeuf ........... A61B 5/14551 600/476 |
| 2016/0331285 A1 | 11/2016 | Choi et al. |
| 2019/0298195 A1* | 10/2019 | De Groot ........... A61B 5/02405 |
| 2020/0146563 A1 | 5/2020 | Lee et al. |
| 2020/0237295 A1 | 7/2020 | Lee et al. |
| 2020/0297955 A1 | 9/2020 | Shouldice |
| 2021/0401303 A1 | 12/2021 | Ogawa et al. |

FOREIGN PATENT DOCUMENTS

| | | |
|---|---|---|
| JP | 2020-146403 A | 9/2020 |
| KR | 10-2016-0133345 A | 11/2016 |
| KR | 10-2020-0094344 A | 8/2020 |
| KR | 10-2020-0139047 A | 12/2020 |

OTHER PUBLICATIONS

Carek et al.; Naptics: Convenient and Continuous Blood Pressure Monitoring during Sleep; Proc. ACM Interact. Mob. Wearable Ubiquitous Technol., vol. 2, No. 3, Article 96. Publication date: Sep. 2018; XP058485292; Sep. 18, 2018.

Radha et al.; Estimating blood pressure trends and the nocturnal dip from photoplethysmography; arXiv:1805.09121v3 [phsyics.med-ph] Dec. 14, 2018; XP080997938; May 23, 2018.

Extended European Search Report dated May 16, 2024; European Appln. No. 22759950.3-1113 / 4233703 PCT/KR2022002103.

* cited by examiner

ELECTRONIC DEVICE AND METHOD FOR PROVIDING INDIVIDUALIZED GUIDE BASED ON BLOOD PRESSURE RELATED INFORMATION

CROSS-REFERENCE TO RELATED APPLICATION(S)

This application is a continuation application, claiming priority under § 365(c), of an International application No. PCT/KR2022/002103, filed on Feb. 11, 2022, which is based on and claims the benefit of a Korean patent application number 10-2021-0024509, filed on Feb. 24, 2021, in the Korean Intellectual Property Office, the disclosure of which is incorporated by reference herein in its entirety.

TECHNICAL FIELD

The disclosure relates to an electronic device that provides an individualized guide based on blood pressure related information. More particularly, the disclosure relates to an electronic device that is worn on a user's body to acquire blood pressure related information and provides an individualized guide based on the acquired information.

BACKGROUND ART

With the development of technology, electronic devices are becoming smaller in size for easy portability and also evolving to perform various functions in various usage forms in response to user's needs. For example, there are various types of wearable devices that can be used while being directly worn on a part of the user's body.

Recently, attempts have been made to obtain various kinds of information from the user's body by utilizing the wearable device directly worn on the user's body and also to provide various services based on the obtained information.

The above information is presented as background information only to assist with an understanding of the disclosure. No determination has been made, and no assertion is made, as to whether any of the above might be applicable as prior art with regard to the disclosure.

DISCLOSURE OF INVENTION

Technical Problem

Aspects of the disclosure are to address at least the above-mentioned problems and/or disadvantages and to provide at least the advantages described below. Accordingly, an aspect of the disclosure is to provide an electronic device and method for acquiring an optical sensor value of a user's body with an optical sensor (e.g., photoplethysmography (PPG)) equipped in the electronic device and offering blood pressure related information calculated from the acquired optical sensor value.

Another aspect of the disclosure is to provide an electronic device and method for providing individualized guide information based on blood pressure related information that is calculated from an optical sensor value obtained by an optical sensor equipped in the electronic device.

The technical issues to be addressed in the disclosure are not limited to the above-mentioned technical problems, and those of ordinary skill in the art to which the disclosure pertains will clearly understand, from the following description, other technical problems not mentioned herein.

Additional aspects will be set forth in part in the description which follows and, in part, will be apparent from the description, or may be learned by practice of the presented embodiments.

Solution to Problem

In accordance with an aspect of the disclosure, an electronic device is provided. The electronic device includes a motion sensor, at least one optical sensor, a processor operatively connected to the motion sensor and the at least one optical sensor, and a memory operatively connected to the processor, wherein the memory stores instructions that cause, when executed, the processor to monitor user state information based on signals received through the motion sensor and the at least one optical sensor, to acquire a sensor value by controlling the at least one optical sensor based on the monitoring, to calculate blood pressure change information according to a user's sleep based on the sensor value, and to provide guide information according to the blood pressure change information.

In accordance with another aspect of the disclosure, a method of an electronic device including a motion sensor and at least one optical sensor is provided. The method includes monitoring user state information based on signals received through the motion sensor and the at least one optical sensor, acquiring a sensor value by controlling the at least one optical sensor based on the monitoring, calculating blood pressure change information according to a user's sleep based on the sensor value, and providing guide information according to the blood pressure change information.

Advantageous Effects of Invention

The electronic device according to various embodiments of the disclosure can be implemented as a wearable device equipped with an optical sensor, thus continuously monitoring a user's body for a long time without inconvenience to a user and measuring a sensor value at a necessary time.

The electronic device according to various embodiments of the disclosure can derive user's sleep related information by calculating and analyzing blood pressure information and blood pressure change information from optical sensor values measured by monitoring a user's body.

The electronic device according to various embodiments of the disclosure can provide an individualized guide based on calculating and analyzing blood pressure information and blood pressure change information from optical sensor values measured by monitoring a user's body.

In addition, various effects explicitly or implicitly appreciated through the disclosure may be provided.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

MODE FOR THE INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
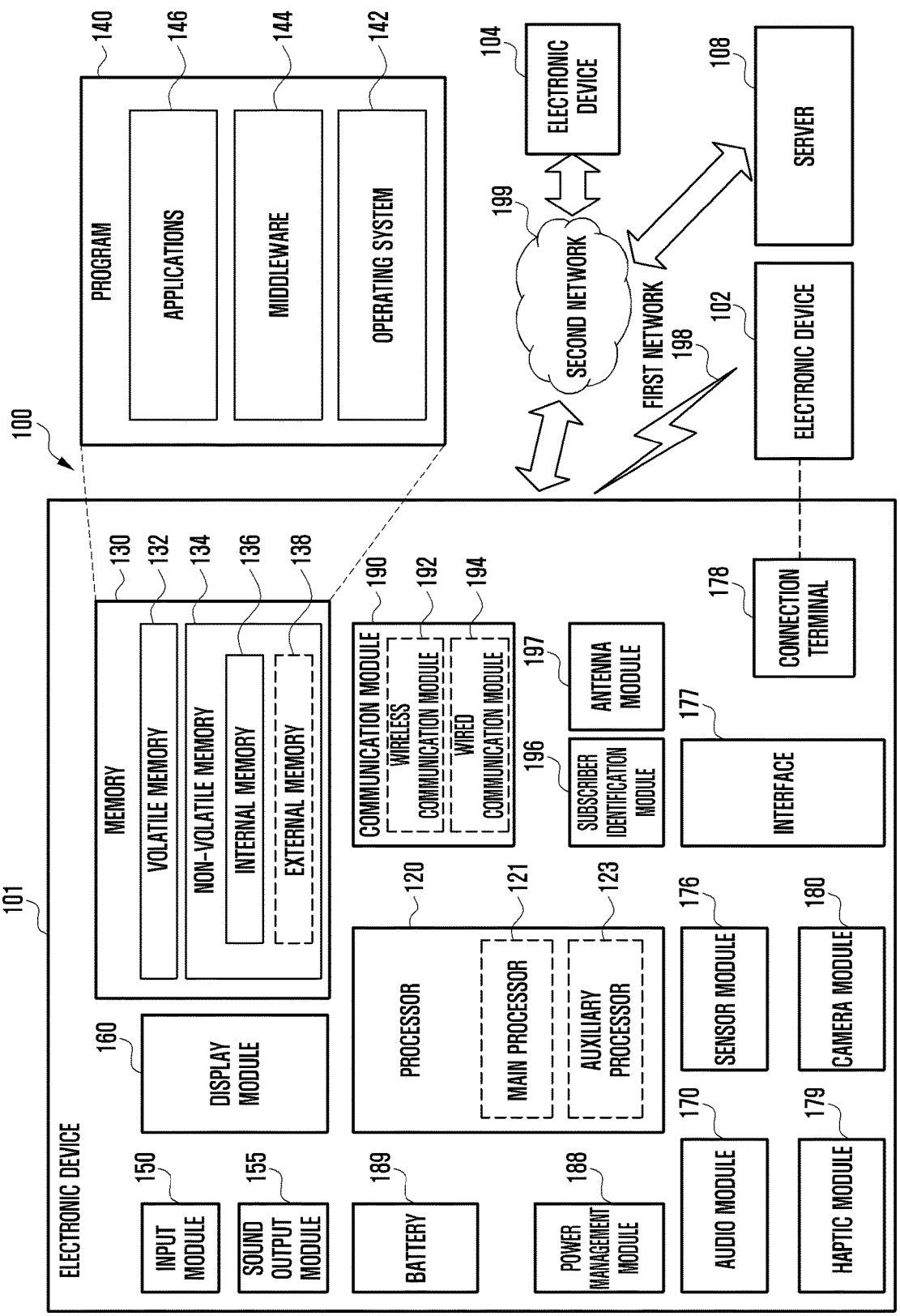
FIG. 1 is a block diagram of an electronic device in a network environment according to an embodiment of the disclosure.

FIG. 1 is a block diagram illustrating an electronic device in a network environment according to an embodiment of the disclosure.

Referring to FIG. 1, an electronic device 101 in a network environment 100 may communicate with an external electronic device 102 via a first network 198 (e.g., a short-range wireless communication network), or at least one of an external electronic device 104 or a server 108 via a second network 199 (e.g., a long-range wireless communication network). According to an embodiment of the disclosure, the electronic device 101 may communicate with the external electronic device 104 via the server 108. According to an embodiment of the disclosure, the electronic device 101 may include a processor 120, a memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments of the disclosure, at least one of the components (e.g., the connecting terminal 178) may be omitted from the electronic device 101, or one or more other components may be added in the electronic device 101. In some embodiments of the disclosure, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment of the disclosure, as at least part of the data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment of the disclosure, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., a sleep) state, or together with the main processor 121 while the main processor 121 is in an active state (e.g., executing an application). According to an embodiment of the disclosure, the auxiliary processor 123 (e.g., an image signal processor or a communication processor) may be implemented as part of another component (e.g., the camera module 180 or the communication module 190) functionally related to the auxiliary processor 123. According to an embodiment of the disclosure, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment of the disclosure, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment of the disclosure, the display module 160 may include a touch sensor adapted to detect a touch, or a pressure sensor adapted to measure the intensity of force incurred by the touch.

The audio module 170 may convert a sound into an electrical signal and vice versa. According to an embodiment of the disclosure, the audio module 170 may obtain the sound via the input module 150, or output the sound via the sound output module 155 or a headphone of an external electronic device (e.g., an external electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment of the disclosure, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the external electronic device 102) directly (e.g., wiredly) or wirelessly. According to an embodiment of the disclosure, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the external electronic device 102). According to an embodiment of the disclosure, the connecting terminal 178 may include, for example, a HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 179 may include, for example, a motor, a piezoelectric element, or an electric stimulator.

The camera module 180 may capture a still image or moving images. According to an embodiment of the disclosure, the camera module 180 may include one or more lenses, image sensors, image signal processors, or flashes.

The power management module 188 may manage power supplied to the electronic device 101. According to one embodiment of the disclosure, the power management module 188 may be implemented as at least part of, for example, a power management integrated circuit (PMIC).

The battery 189 may supply power to at least one component of the electronic device 101. According to an embodiment of the disclosure, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the external electronic device 102, the external electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment of the disclosure, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a $5^{th}$ generation (5G) network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4th generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the millimeter (mm) Wave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the external electronic device 104), or a network system (e.g., the second network 199). According to an embodiment of the disclosure, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment of the disclosure, the antenna module 197 may include an antenna including a radiating element including a conductive material or a conductive pattern formed in or on a substrate (e.g., a printed circuit board (PCB)). According to an embodiment of the disclosure, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment of the disclosure, another component (e.g., a radio frequency integrated circuit (RFIC)) other than the radiating element may be additionally formed as part of the antenna module 197.

According to various embodiments of the disclosure, the antenna module 197 may form a mmWave antenna module. According to an embodiment of the disclosure, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 101 and the external electronic device 104 via the server 108 coupled with the second network 199. Each of the external electronic devices 102 or 104 may be a device of a same type as, or a different type, from the electronic device 101. According to an embodiment of the disclosure, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment of the disclosure, the external electronic device 104 may include an internet-of-things (IoT) device. The server 108 may be an intelligent server using machine learning and/or a neural network. According to an embodiment of the disclosure, the external electronic device 104 or the server 108 may be included in the second network 199. The electronic device 101 may be applied to intelligent services (e.g., a smart home, a smart city, a smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 140) including one or more instructions that are stored in a storage medium (e.g., an internal memory 136 or an external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities, and some of the multiple entities may be separately disposed in different components. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

Figure 2A:
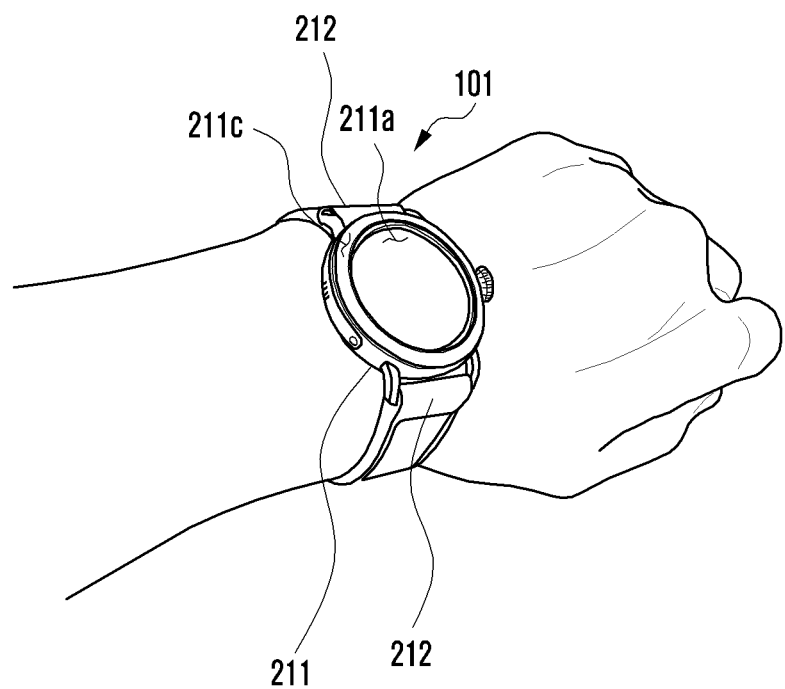
FIGS. 2A and 2B are diagrams illustrating an outward appearance of an electronic device having an optical sensor according to various embodiments of the disclosure.
Figure 2B:
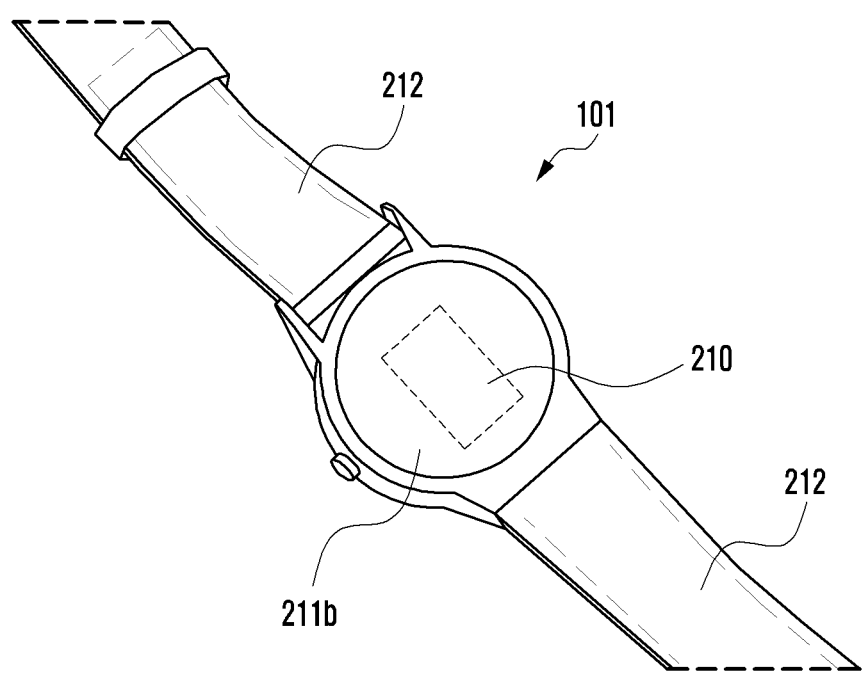

FIGS. 2A and 2B are diagrams illustrating an outward appearance of an electronic device (e.g., the electronic device 101 in FIG. 1) according to various embodiments of the disclosure. FIG. 2A is a perspective view, and FIG. 2B is a rear view.

Referring to FIGS. 2A and 2B, in various embodiments of the disclosure, the electronic device 101 (e.g., a wearable device, hereinafter referred to as the wearable device) may include an electronic device worn on a user's wrist. This is, however, not construed as a limitation. The wearable device 101 may include various types of portable electronic devices equipped with an optical sensor (e.g., a photoplethysmography (PPG) sensor) and capable of acquiring user's biometric information in a state of being at least partially in contact with the user's body. For example, the wearable device 101 may be implemented as various wearable device types, such as a body-attachable device (e.g., health patch, digital tattoo), a clothing-type device (e.g., smart clothing, gloves), or a band-type device (e.g., wrist/arm/finger bands, smart ring), each of which is capable of extracting user's biometric information through a skin region in which blood vessels are located, while maintaining at least partial contact with the user's body when this device is worn by the user.

According to various embodiments of the disclosure, the wearable device 101 may include the optical sensor 210 (e.g., the PPG sensor) mounted therein for extracting user's biometric data. For example, a region in which the optical sensor 210 is disposed may maintain a state of being at least partially in close contact with the user's body, and a detection area of the optical sensor 210 may be formed to correspond to the skin where the user's blood vessels are located.

Referring to FIGS. 2A and 2B, the wearable device 101 may include a housing 211 having a first surface (or front surface) 211a, a second surface (or rear surface) 211b, and a side surface 211c surrounding a space between the first surface 211a and the second surface 211b, and a fastening member 212 (e.g., a strap) connected to at least a portion of the housing 211 and configured to be attachable to and detachable from a user's body part (e.g., wrist or ankle).

According to various embodiments of the disclosure, the first surface 211a may be formed at least in part by a substantially transparent front plate (e.g., a glass plate having various coating layers, or a polymer plate).

According to various embodiments of the disclosure, the second surface 211b may be formed by a substantially opaque rear plate. The rear plate may be formed of, for example, coated or colored glass, ceramic, polymer, metal (e.g., aluminum, stainless steel (STS), or magnesium), or any combination thereof. The second surface (e.g., the rear surface) 211b of the wearable device 101 may be a surface in direct contact with the user's body.

According to various embodiments of the disclosure, the side surface 211c is partially combined with the front plate (e.g., the first surface 211a) and the rear plate (e.g., the second surface 211b) and may be formed by a side bezel structure (or "lateral member") having metal and/or polymer.

According to various embodiments of the disclosure, the rear plate and the side bezel structure may be integrally formed and include the same material (e.g., a metal material, such as aluminum). The fastening member 212 may be formed of various materials in various shapes. For example, a woven fabric, leather, rubber, urethane, metal, ceramic, or any combination thereof may be used in an integral shape or in the shape of a plurality of unit links connected flexibly to each other.

According to various embodiments of the disclosure, the wearable device 101 may include the optical sensor 210 for measuring a user's blood pressure. For example, the optical sensor 210 may be at least partially disposed on the second surface 211b of the wearable device 101 and thereby contact the user's body at least in part. For example, the wearable device 101 may utilize, as a detection area, a partial area corresponding to a position where the optical sensor 210 is disposed. For example, the detection area of the optical sensor 210 may include a region in direct contact with the user's body when the wearable device 101 is worn, and may be formed to correspond to the skin where the user's blood vessels are located. According to various embodiments of the disclosure, the optical sensor 210 may also be partially disposed even in the fastening member 212 other than the housing 211 of the wearable device 101. For example, the arrangement position of the optical sensor 210 may not be limited to the housing 211.

According to various embodiments of the disclosure, the optical sensor 210 may include the PPG sensor (e.g., a pulse wave sensor). For example, the PPG sensor may acquire a sensor value (e.g., a raw sensor signal) by emitting light to a skin surface where blood vessels are located and receiving reflected light of the emitted light. For example, the wearable device 101 may identify various kinds of biometric information, such as heart rate information, stress information, and sleep information of the user, based on the acquired sensor value.

According to various embodiments of the disclosure, the wearable device 101 may measure the user's blood pressure, based on the sensor value. For example, in measuring the blood pressure, the optical sensor 210 may extract a feature value corresponding to the user's biometric data, based on pulses collected from the sensor value. For example, the wearable device 101 may compare the feature value extracted using the optical sensor 210 with predetermined reference biometric data and, based on a difference value according to a comparison result, obtain the user's blood pressure.

Figure 3:
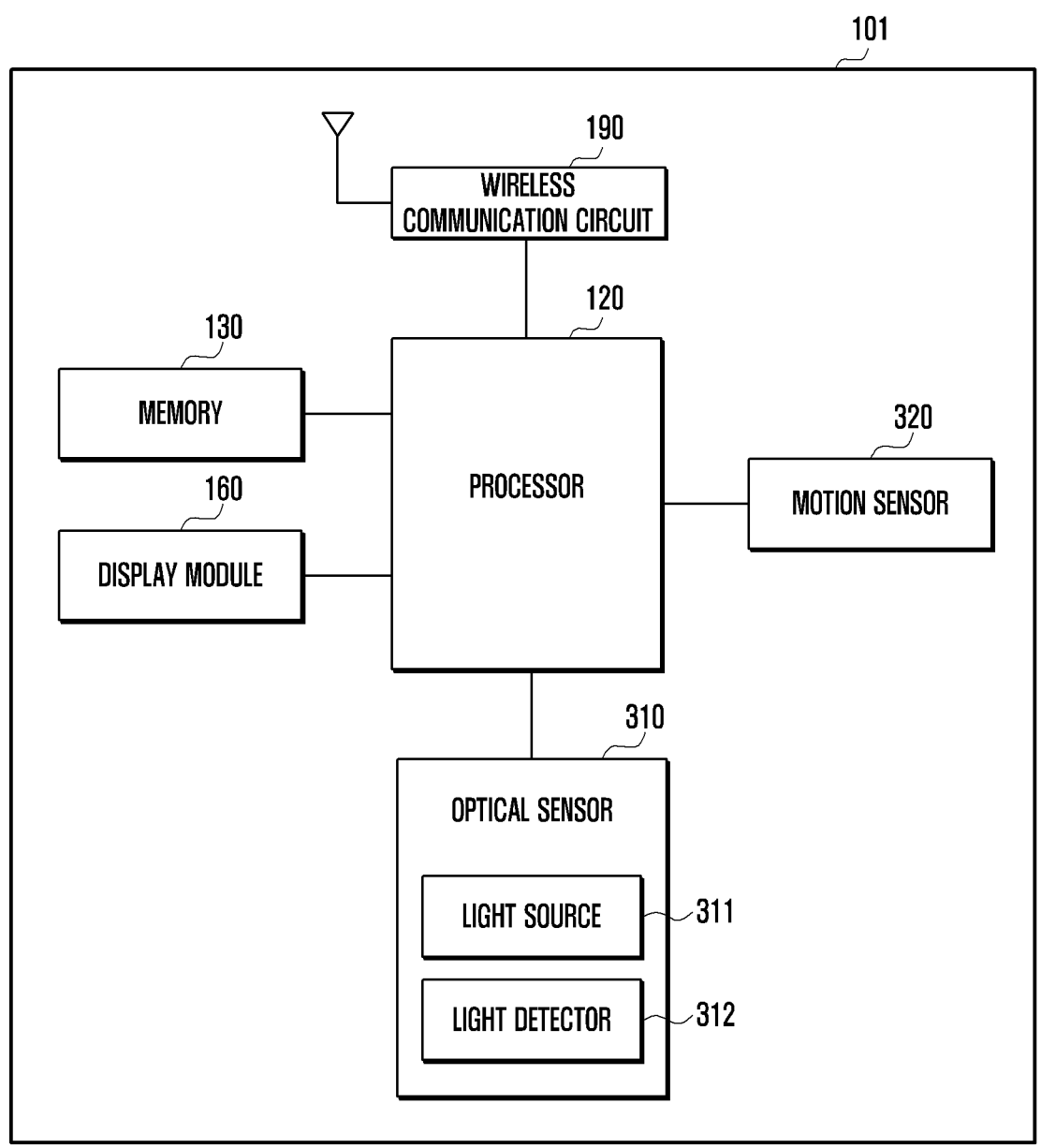
FIG. 3 is a block diagram of an electronic device having an optical sensor according to an embodiment of the disclosure.

FIG. 3 is a block diagram of an electronic device according to an embodiment of the disclosure.

Referring to FIG. 3, the electronic device 101 (e.g., a wearable device, hereinafter, referred to as the wearable device) may include a processor (e.g., the processor 120 in FIG. 1), a memory (e.g., the memory 130 in FIG. 1), a display module (e.g., the display module 160 in FIG. 1), a wireless communication circuit (e.g., the communication module 190 in FIG. 1), an optical sensor 310 (e.g., the sensor module 176 in FIG. 1 or the optical sensor 210 in FIG. 2B), and/or a motion sensor 320 (e.g., the sensor module 176 in FIG. 1). The components shown in FIG. 3 may be omitted, replaced, or integrated as one module in various embodiments. Redundant descriptions of components described above with reference to FIG. 1 among the components shown in FIG. 3 may be omitted hereinafter.

According to various embodiments of the disclosure, the wearable device 101 may measure the user's blood pressure by using the optical sensor 310. For example, the optical sensor 310 may include the photoplethysmography (PPG) sensor for acquiring the user's biometric data.

According to various embodiments of the disclosure, the optical sensor 310 may include a light source 311 that emits light, and a light detector (e.g., photo detector, PD) 312 that receives reflected light of the emitted light.

According to various embodiments of the disclosure, the light source 311 and the light detector 312 of the optical sensor 310 may be disposed to correspond to a detection area for measuring the blood pressure and may be driven in a state of being at least partially in contact with the skin where the user's blood vessels are located. For example, the light source 311 may emit light toward the skin where the user's blood vessels are located. A portion of the emitted light may be partially absorbed by the user's skin or blood vessels, and the remaining portion may be reflected or scattered through the user's body to generate reflected light.

Generally, the amount of blood flow flowing through the blood vessels may fluctuate with time. For example, light emitted toward the skin where the user's blood vessels are located may be partially absorbed by the user's skin or blood vessels. For example, the amount of light absorbed by the blood vessels may fluctuate according to fluctuations in the amount of blood flow. For example, the blood vessels can absorb a lot of light when the amount of blood flow is high, and can absorb less light when the amount of blood flow is low.

According to various embodiments of the disclosure, based on the sensor value outputted by the optical sensor 310 receiving the reflected light through the light detector 312, the processor 120 may extract sensor data including the amount of fluctuation in blood flow. For example, the optical sensor 310 may receive the reflected light through the light detector 312 and output the sensor value corresponding to the received reflected light (e.g., light scattered or reflected from a region of the skin where blood vessels are located). For example, the processor 120 may extract the user's biometric data (e.g., cardiac output (CO), total peripheral resistance (TPR), and biometric parameters), based on the sensor value. For example, the processor 120 may analyze the sensor value and thereby estimate a change in intensity of the reflected light over time.

According to various embodiments of the disclosure, the processor 120 may extract the user's biometric data by analyzing the sensor value and estimating a fluctuation in the reflected light corresponding to a change in the volume of the user's blood vessel (e.g., a blood vessel located in a finger or wrist, a radial artery below a wrist). For example, the processor 120 may extract the user's biometric data, based on a correlation between the volume change and the change amount of the reflected light in the sensor value.

According to various embodiments of the disclosure, the light source 311 and/or the light detector 312 may be configured in plurality. For example, the light source 311 may include a plurality of light emitters capable of emitting light (e.g., red, green, blue, and/or IR) of the same or different wavelengths, respectively. For example, the light source 311 may include at least one of a light emitting diode (LED), an organic light emitting diode (OLED), a semiconductor laser diode (LD), a solid laser, or an infrared (IR) diode.

For example, the light source 311 may output a blue light having a wavelength of about 400 nm to about 550 nm, a green light having a wavelength of about 450 nm to about 650 nm, a red light having a wavelength of about 550 nm to about 700 nm, and/or an infrared (IR) light having a wavelength of about 880 nm to about 940 nm. For example, the light detector 312 may include a plurality of light receiving elements (e.g., photo diodes (PDs)). For example, other than the photo diode (PD), the light detector 312 may include at least one of an avalanche photo diode (APD), a photo transistor, or an image sensor. According to various embodiments of the disclosure, the motion sensor 320 may include various types of sensors, such as a gyro sensor and an acceleration sensor, capable of detecting the movement of the wearable device 101. For example, the motion sensor 320 may be electrically connected to the processor 120 and provide the processor 120 with a sensor value (e.g., a motion signal) generated in response to detecting the motion of the wearable device 101.

According to various embodiments of the disclosure, the processor 120 may identify user state information by using the optical sensor 310 and/or the motion sensor 320. For example, the user state information may include information on whether the user is in a daily activity state or a sleep state. For example, when the user is in a daily activity state, the user state information may include information on whether the user is in an active state or an inactive state during daily activities. For example, when the user is in a sleep state, the user state information may include sleep stage information indicating a stage according to the depth of sleep, such as a deep sleep stage or a shallow sleep stage (e.g., a rapid eye movement, REM).

According to various embodiments of the disclosure, the processor 120 may measure a signal corresponding to the movement of the wearable device 101 for a specific time by using the acceleration sensor and/or the gyro sensor included in the motion sensor 320 and, based on the measured signal, identify the user state information. For example, when the magnitude of a signal outputted from the motion sensor 320 is greater than or equal to a predetermined threshold, or when a signal value greater than or equal to a predetermined threshold is frequently outputted over a predetermined frequency for a specific time, the processor 120 may determine that the user is in the daily activity state. For example, when the magnitude of a signal outputted from the motion sensor 320 is maintained below a predetermined threshold for a specific time, the processor 120 may determine that the user in the inactive state or the sleep state. For the signal of the motion sensor 320, the threshold value and/or the frequency number may be determined, for example, as experimental values according to the stage of daily activity, daily inactivity, or sleep, and may also be changed through user's state monitoring and/or user's feedback.

According to various embodiments of the disclosure, the processor 120 may identify the user state information, based on a signal measured through the optical sensor 310. For example, the processor 120 may acquire a heart rate (HR) and/or a heart rate variation (HRV) from the signal measured through the optical sensor 310 and, based on this, identify the state information indicating whether the user is in the sleep state or in the daily activity state. For example, the processor 120 may analyze the heart rate and/or the heart rate variation acquired based on the signal outputted through the optical sensor 310 and, when a pattern of the heart rate and/or the heart rate variation according to sleep, daily activity, or daily inactivity is extracted, determine it as the sleep state, the daily active state, or the daily inactive state. For example, the pattern of the heart rate and/or the heart rate variation may be determined, for example, as experimental values according to the stage of daily activity, daily inactivity, or sleep, and may also be changed through user's state monitoring and/or user's feedback.

According to various embodiments of the disclosure, the processor 120 may monitor the user state information, based on a sensor value detected through the optical sensor 310 and/or the motion sensor 320. Then, based on this, the processor 120 may extract biometric data by using the optical sensor 310 and acquire user's blood pressure information based on the extracted biometric data.

According to various embodiments of the disclosure, by executing a program (e.g., the program 140 in FIG. 1) stored in the memory 130, the processor 120 may control at least one other component (e.g., a hardware or software component) and perform various data processing or operations. According to various embodiments of the disclosure, the processor 120 may extract biometric data related to the user by driving the optical sensor 310 and acquire blood pressure information from the extracted biometric data by using a blood pressure measurement algorithm stored in the memory 130. For example, the processor 120 may estimate the user's blood pressure by extracting a pulse wave from a sensor value outputted through the optical sensor 310 and extracting feature points through a pulse wave analysis on the waveform of the pulse wave indicating a change according to cardiac output and blood vessel resistance. For example, the processor 120 may estimate the user's blood pressure by extracting a pulse wave period from a plurality of sensor values outputted through the optical sensor 310 and calculating a pulse wave velocity.

According to various embodiments of the disclosure, in order to calculate more accurate blood pressure information, the processor 120 may compare the extracted biometric data with reference biometric data (e.g., reference blood pressure data) previously stored in the memory 130. For example, the reference blood pressure data may include learning data constructed through accumulated learning for the user's blood pressure data acquired using the optical sensor 310. For example, the reference blood pressure data may include learning data for blood pressure data corrected based on a user's absolute blood pressure value measured using a cuff-type blood pressure gauge. For example, the processor 120 may acquire a user's current blood pressure value by obtaining the user's biometric data from a sensor value outputted through the optical sensor 310 and comparing and analyzing it with the reference blood pressure data previously stored in the memory 130.

According to various embodiments of the disclosure, the wearable device 101 may periodically and repeatedly acquire the user's biometric data. For example, the processor 101 may control the optical sensor 310 at a specific period and/or at a specific time to acquire the user's biometric data and acquire the user's blood pressure information. For example, the processor 120 may monitor the user state information by using the optical sensor 310 and/or the motion sensor 320 and, based on this, control the optical sensor 310 at a specific period and/or at a specific time to acquire the user's biometric data and acquire the user's blood pressure information.

According to various embodiments of the disclosure, the wearable device 101 may extract various types of blood pressure related information by analyzing the acquired user's blood pressure information. For example, the blood pressure related information may include blood pressure change information according to sleep. For example, the blood pressure change information according to sleep may include the presence or absence of a blood pressure drop (dipper) according to sleep, the degree of the blood pressure drop (e.g., % level), the pattern of a blood pressure drop interval, a blood pressure drop pattern that enters the blood pressure drop interval, and/or a blood pressure rise pattern that leaves the blood pressure drop interval.

For example, the presence or absence of the blood pressure drop may be determined based on a difference between an average blood pressure value in the daily activity state (hereinafter referred to as a daily average blood pressure) and an average blood pressure value in the sleep state (hereinafter referred to as a sleep average blood pressure). For example, the average blood pressure value may be calculated based on the systolic blood pressure. For example, in case of the presence or absence of the blood pressure drop, if the sleep average blood pressure decreases by, e.g., 10% or more as a result of comparing the daily average blood pressure and the sleep average blood pressure, it may be determined that the blood pressure drop is present. For example, in case of the degree of the blood pressure drop, as a result of comparing the daily average blood pressure and the sleep average blood pressure, a decrease of 10% or more in the sleep average blood pressure may be determined as a low-level blood pressure drop (dipper), a decrease of 20% or more may be determined as a high-level blood pressure drop (extreme dipper), and a daily average blood pressure higher than the sleep average blood pressure may be determined as a reverse-level blood pressure drop (reverse dipper).

For example, the pattern of the blood pressure drop interval may include information calculated by extracting the blood pressure feature points within the blood pressure drop interval and analyzing their pattern. The blood pressure drop interval refers to the period of time in which a drop in blood pressure occurs during the user's sleep. The blood pressure feature points may be a change in the length of the blood pressure drop interval or a change in blood pressure within the blood pressure drop interval.

For example, the blood pressure drop/rise pattern may include a change characteristic of a section entering a sleep state from a daily activity state or a section entering a daily activity state from a sleep state. For example, the blood pressure drop/rise pattern may include information on the interval of this section and/or the amount of change in blood pressure with respect to the interval of the corresponding section.

According to various embodiments of the disclosure, the processor 120 may monitor the user state information through the optical sensor 310 and/or the motion sensor 320 and acquire the user's biometric data by driving the optical sensor 310 in a driving method set based on the user state information in a period and/or at a time point set according to the user state information. For example, depending on the state information, the processor 120 may change the driving method of the optical sensor 310 including the setting of the driving timing or time point, the light intensity, and/or the light wavelength.

According to various embodiments of the disclosure, the processor 120 may monitor the user state information through the optical sensor 310 and/or the motion sensor 320 and, depending on the user state information, change a driving method for the monitoring of the optical sensor 310 and/or the motion sensor 320 and/or a driving method for the biometric data measurement of the optical sensor 310. For example, depending on the state information, the processor 120 may change the driving method of the optical sensor 310 including the setting of the driving timing, the light intensity, and/or the light wavelength.

For example, if detecting the user state information as a sleep state while monitoring the user state information through the optical sensor 310 and/or the motion sensor 320, the processor 120 may decrease a monitoring frequency by increasing a monitoring period of the optical sensor 310 and/or the motion sensor 320 (e.g., from an interval of 5 minutes to an interval of 10 minutes). For example, when the user state information is detected as a sleep state, the processor 120 may reduce the frequency of measuring biometric data through the optical sensor 310. For example, when the user state information is detected as a sleep state, the processor 120 may monitor a user's movement and/or a sleep stage according to a sleep depth through the optical sensor 310 and/or the motion sensor 320 and, if the user enters a deep sleep stage and/or a REM sleep stage, may control the optical sensor 310 to acquire biometric data and calculate blood pressure information. For example, when the user state information is detected as a sleep state, the processor 120 may control the optical sensor 310 so that the light source 311 emits light of a wavelength band (e.g., IR wavelength) that is less disturbing to sleep and less sensitive to movement. For example, when the user state information is detected as a sleep state, the processor 120 may lower a current and/or a gain supplied to the optical sensor 310 to reduce power consumption.

For example, if detecting the user state information as a daily activity state while monitoring the user state information through the optical sensor 310 and/or the motion sensor 320, the processor 120 may increase a monitoring frequency by decreasing a monitoring period of the optical sensor 310 and/or the motion sensor 320 (e.g., from a 10-minute interval to a 5-minute interval). For example, when the user state information is detected as a daily activity state, the processor 120 may increase the frequency of measuring biometric data through the optical sensor 310. For example, when the user state information is detected as a daily activity state, the processor 120 may monitor a user's movement and/or activity state through the optical sensor 310 and/or the motion sensor 320 and, if the user enters an inactive state, may control the optical sensor 310 to acquire biometric data and calculate blood pressure information. For example, when the user state information is detected as a daily activity state, the processor 120 may control the optical sensor 310 so that the light source 311 emits light of a wavelength band (e.g., blue wavelength) that is strong to movement. For example, when the user state information is detected as a daily activity state, the processor 120 may increase a current and/or a gain supplied to the optical sensor 310 to increase a measurement success rate.

According to various embodiments of the disclosure, the display module 160 may provide various types of visual information related to the biometric information acquired by the processor 120. For example, the display module 160 may display various types of visual information generated based on the biometric information or a visual notification required in connection with the acquisition of the biometric information.

According to various embodiments of the disclosure, the wearable device 101 may perform wireless communication with an external electronic device (e.g., the external electronic device 102 or 104 in FIG. 1) through the wireless communication circuit (e.g., the communication module 190 in FIG. 1). For example, the wearable device 101 may perform wireless communication with a portable electronic device (e.g., a smartphone) and exchange commands and/or data (e.g., user state information, biometric data, blood pressure information, and/or blood pressure change information). According to various embodiments of the disclosure, the wearable device 101 may be controlled at least in part by an external electronic device. For example, the wearable device 101 may perform at least one function under the control of an external electronic device. For example, the wearable device 101 may jointly perform at least one function by interworking with an external electronic device.

Figure 4:
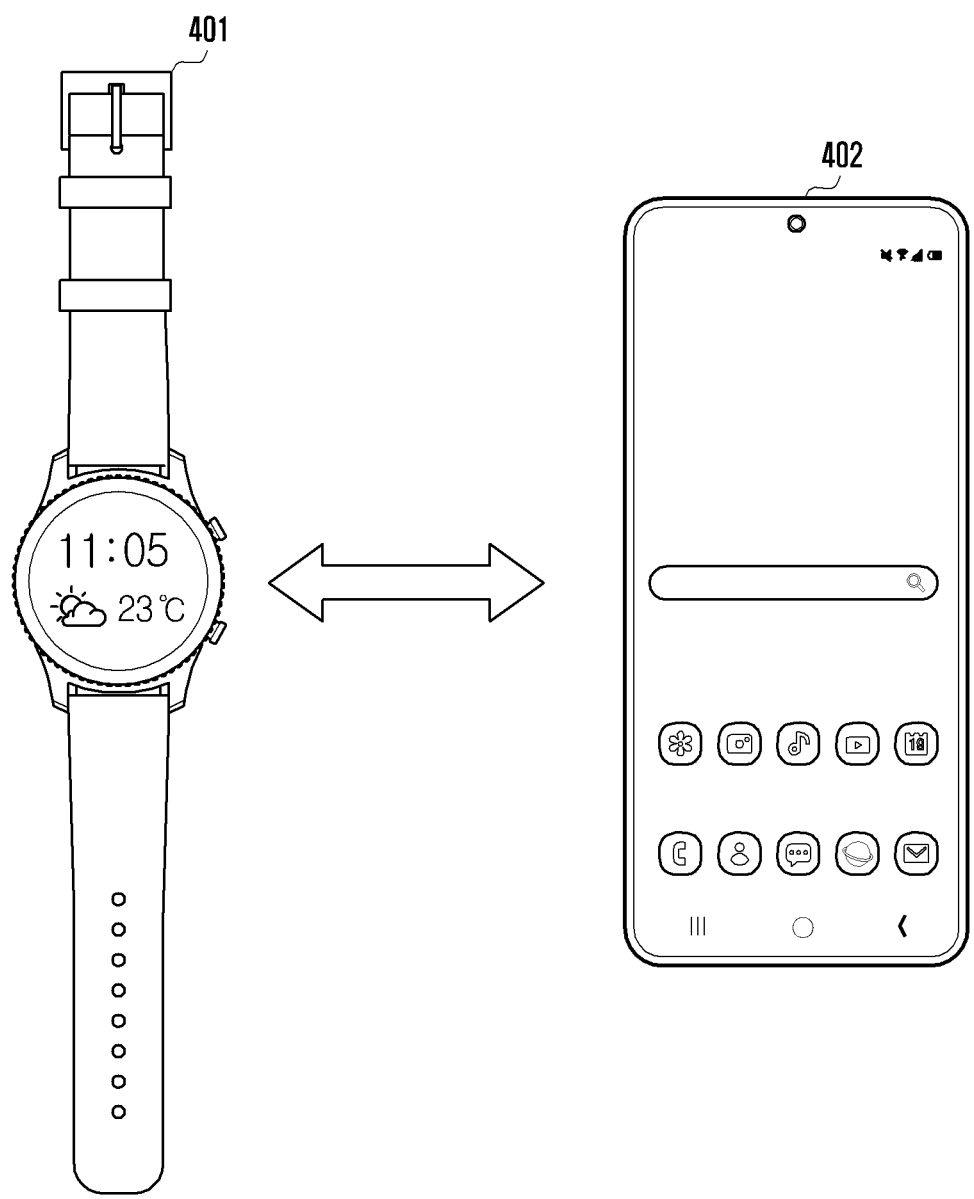
FIG. 4 is a diagram illustrating an interworking operation between an electronic device having an optical sensor and an external electronic device according to an embodiment of the disclosure.

FIG. 4 is a diagram illustrating an interworking operation between an electronic device and an external electronic device according to an embodiment of the disclosure.

Referring to FIG. 4, a first electronic device 401 (e.g., the electronic device 101 in FIG. 1 or the wearable device 101 in FIG. 2A, 2B, or 3) according to various embodiments may perform wireless communication with a second electronic device 402 (e.g., a smartphone) which is an external electronic device. For example, the first electronic device 401 and the second electronic device 402 may perform communication through a wireless communication scheme and thereby share commands and/or data (e.g., user state information, sensor values (raw data), biometric data, or blood pressure related information including blood pressure information and blood pressure change information). For example, the first electronic device 401 may transmit at least part of the user state information and the blood pressure related information including the blood pressure information and the blood pressure change information to the second electronic device 402 and receive user guide information from the second electronic device 402 through a wireless communication circuit (e.g., the communication module 190 in FIG. 1 or the wireless communication circuit 190 in FIG. 3). According to various embodiments of the disclosure, the second electronic device 402 may include at least some of the components of the electronic device 101 shown in FIG. 1.

According to various embodiments of the disclosure, the first electronic device 401 may be controlled at least in part by the second electronic device 402. For example, the second electronic device 402 may control at least in part a function performed by the first electronic device 401. For example, the first electronic device 401 may receive a control command from the second electronic device 402 through a wireless communication scheme.

According to various embodiments of the disclosure, the first electronic device 401 and the second electronic device 402 may interwork with each other to execute at least one program or function at substantially the same time. For example, the second electronic device 402 may control the first electronic device 401 such that the first electronic device 401 acquires and monitors the user state information by using the optical sensor (e.g., the optical sensor 310 in FIG. 3) and/or the motion sensor (e.g., the motion sensor 320 in FIG. 3) and, based on the user state information, extracts the user's biometric data by operating the optical sensor 310. For example, the first electronic device 401 may be controlled to transmit the user state information acquired through the optical sensor 310 and/or the motion sensor 320 and/or the sensor value or the user's biometric data acquired through the optical sensor 310 to the second electronic device 402. For example, the second electronic device 402 may calculate the blood pressure related information including the blood pressure information and the blood pressure change information by analyzing the received sensor value or biometric data and then transmit at least part of the guide information based on the blood pressure related information to the first electronic device 401 such that the user guide information is provided through at least one of the first electronic device 401 and the second electronic device 402.

According to various embodiments of the disclosure, an electronic device (e.g., the electronic device 101 or 401 in FIG. 1, FIG. 2A, FIG. 2B, FIG. 3, or FIG. 4) may include a motion sensor (e.g., the motion sensor 320 in FIG. 4), at least one optical sensor (e.g., the optical sensor 210 in FIG. 2B or the optical sensor 310 in FIG. 4), a processor (e.g., the processor 120 in FIG. 1 or FIG. 4) operatively connected to the motion sensor 320 and the at least one optical sensor 210 or 310, and a memory (e.g., the memory 130 in FIG. 1 or FIG. 4) operatively connected to the processor 120. The memory 130 may store instructions that cause, when executed, the processor 120 to monitor user state information based on signals received through the motion sensor 320 and the at least one optical sensor 210 or 310, to acquire a sensor value by controlling the at least one optical sensor 210 or 310 based on the monitoring, to calculate blood pressure change information according to a user's sleep based on the sensor value, and to provide guide information according to the blood pressure change information.

According to various embodiments of the disclosure, the processor 120 may be configured to identify whether the user is in a daily activity state or a sleep state, depending on the user state information, and to drive the at least one optical sensor 210 or 310 by adjusting at least one of a driving timing, an output light intensity, and an output light wavelength, based on the user state information.

According to various embodiments of the disclosure, the processor 120 may be configured to calculate blood pressure values based on sensor values acquired from the at least one optical sensor for a specified time and calculate the blood pressure change information by extracting feature points from the blood pressure values.

According to various embodiments of the disclosure, the processor 120 may be configured to analyze the feature points and thereby calculate the blood pressure change information according to sleep including at least one of a presence or absence of a blood pressure drop according to sleep, a degree of the blood pressure drop, a pattern of a blood pressure drop interval, a blood pressure drop pattern entering the blood pressure drop interval, and a blood pressure rise pattern leaving the blood pressure drop interval.

According to various embodiments of the disclosure, the processor 120 may be configured to determine the guide information to be provided to the user, based on the blood pressure change information according to sleep, and to provide the guide information at a time point determined based on the blood pressure rise pattern leaving the blood pressure drop interval.

According to various embodiments of the disclosure, the processor 120 may be configured to provide the guide information in a form of at least one of a screen including text or images, audio including voice or sound, or vibration.

According to various embodiments of the disclosure, the processor 120 may be configured to analyze a change trend of the feature points and extract, as the blood pressure drop interval according to sleep, an interval maintained for a specified period after the blood pressure is relatively low.

According to various embodiments of the disclosure, the processor 120 may be configured to calculate the degree of a blood pressure drop according to sleep by comparing an average blood pressure value of the blood pressure drop interval with an average blood pressure value of an interval other than the blood pressure drop interval.

According to various embodiments of the disclosure, the processor 120 may be configured to monitor the user state information by acquiring at least one of a heart rate (HR) or a heart rate variation (HRV) from the signal received through the at least one optical sensor 210 or 310.

According to various embodiments of the disclosure, the processor 120 may be configured to monitor the user state information by analyzing at least one of a magnitude or a frequency of the signal received through the motion sensor.

Figure 5:
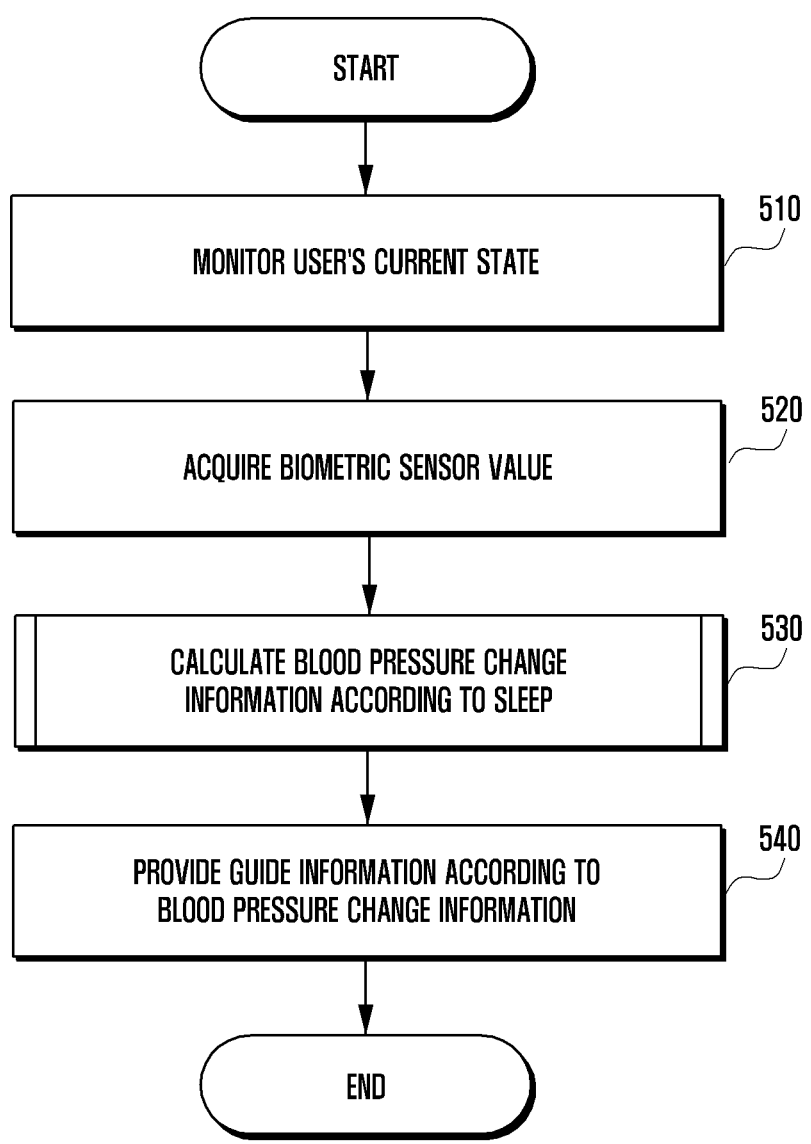
FIG. 5 is a flow diagram illustrating an operation of an electronic device having an optical sensor according to an embodiment of the disclosure.

FIG. 5 is a flow diagram illustrating an operation of an electronic device (e.g., the electronic device 101 in FIGS. 1, 2A, 2B, and/or FIG. 3, or the electronic device 401 in FIG. 4) having an optical sensor according to an embodiment of the disclosure. Hereinafter, detailed descriptions of operations overlapping those of the electronic device 101 previously described with reference to FIGS. 1, 2A, 2B, 3, and/or FIG. 4 may be omitted.

Referring to FIG. 5, at operation 510, a processor (e.g., the processor 120 in FIG. 1 or FIG. 3) may monitor a user's current state by determining user state information through an optical sensor (e.g., the optical sensor 310 in FIG. 3) and/or a motion sensor (e.g., the motion sensor 320 in FIG. 3).

For example, the user state information may include a daily activity state or a sleep state. For example, when the user is in a daily activity state, the state information may include an active state or an inactive state during daily activities. For example, when the user is in a sleep state, the state information may include sleep stage information according to the depth of sleep.

According to various embodiments of the disclosure, the processor 120 may measure a sensor value corresponding to the movement of the electronic device 101 for a predetermined time through an acceleration sensor and/or a gyro sensor included in the motion sensor 320 and, based on the measured sensor value, identify the user state information.

According to various embodiments of the disclosure, the processor 120 may acquire, for example, a heart rate (HR) and/or a heart rate variation (HRV) based on biometric data extracted from the sensor value measured through the optical sensor 310 and, based on this, identify the state information indicating whether the user is in a sleep state or a daily activity state.

According to various embodiments of the disclosure, the processor 120 may identify the user state information based on the sensor value detected through the optical sensor 310 and/or the motion sensor 320 and thereby monitor the user's current state.

According to various embodiments of the disclosure, at operation 520, the processor 120 may acquire a sensor value by driving the optical sensor 310, based on the user state information. For example, depending on the state information, the processor 120 may change a driving method of the optical sensor 310 including the setting of driving timing, light intensity, and/or light wavelength.

For example, when the user state information is a sleep state, the processor 120 may increase a period of measuring biometric data through the optical sensor 310 or decrease a measurement frequency (e.g., every 5 minutes to every 10 minutes). For example, when the user state information is a sleep state, the processor 120 may control the optical sensor 310 to emit light of a wavelength band (e.g., IR wavelength) that is less disturbing to sleep.

For example, when the user state information is in a daily activity state, the processor 120 may decrease a period of measuring biometric data through the optical sensor 310 or increase a measurement frequency (e.g., every 10 minutes to every 5 minutes). For example, when the user state information is a daily activity state, the processor 120 may monitor a user's movement and/or activity state through the optical sensor 310 and/or the motion sensor 320 and, if the user enters an inactive state, may control the optical sensor 310 to acquire a sensor value. For example, when the user state information is a daily activity state, the processor 120 may cause the optical sensor 310 to emit light of a wavelength band (e.g., blue wavelength) that is strong to movement. For example, when the user state information is a daily activity state, the processor 120 may increase a current and/or a gain supplied to the optical sensor 310 to increase a measurement success rate.

According to various embodiments of the disclosure, at operation 530, the processor 120 may extract biometric data from the sensor value acquired through the optical sensor 310, calculate user's blood pressure information based on the extracted biometric data, and analyze the blood pressure information acquired for a specified time (e.g., 24 hours), thereby calculating blood pressure related information including blood pressure change information according to sleep.

Figure 6:
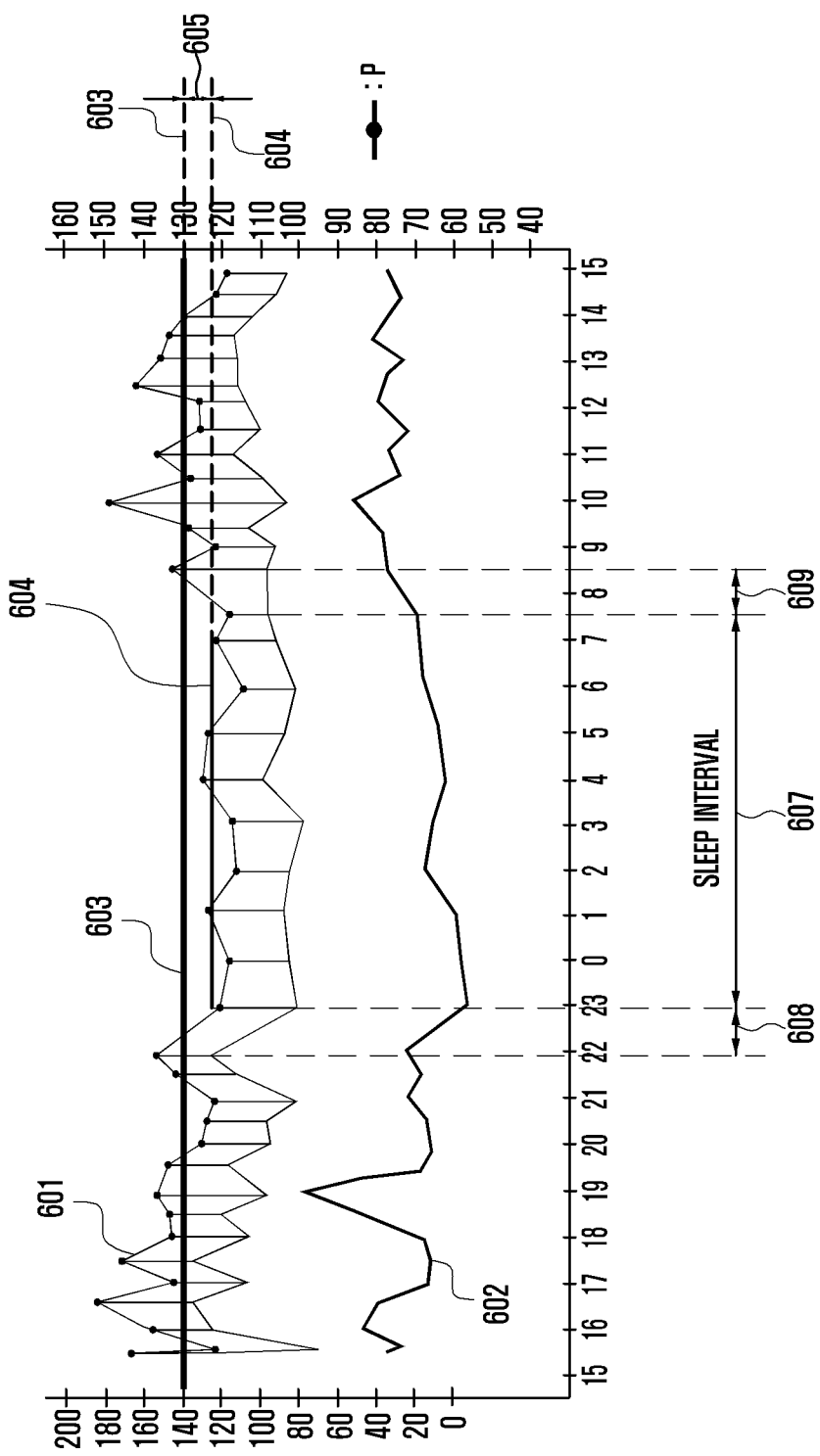
FIG. 6 is a diagram illustrating an operation of calculating blood pressure change information according to sleep from a sensor value measured by an optical sensor of an electronic device according to an embodiment of the disclosure.
Figure 7:
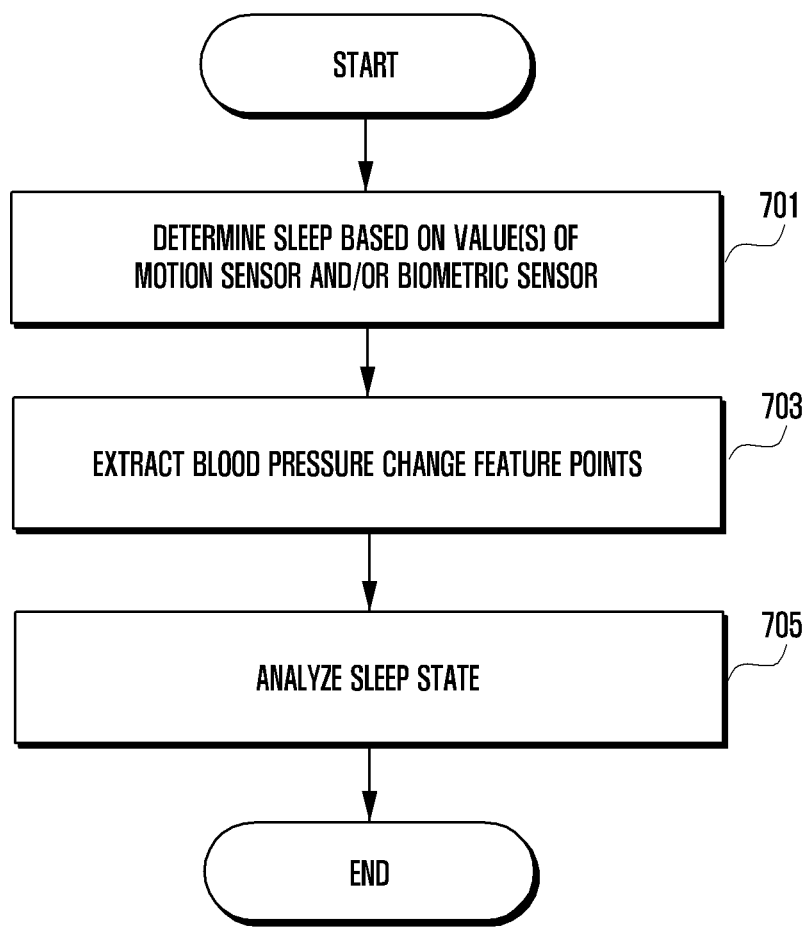
FIG. 7 is a flow diagram illustrating an operation of calculating blood pressure change information according to sleep in an electronic device according to an embodiment of the disclosure.

FIG. 6 is a diagram illustrating an operation of calculating blood pressure change information according to sleep from a sensor value measured by an optical sensor (e.g., the optical sensor 310 in FIG. 3) of an electronic device (e.g., the electronic device 101 in FIGS. 1, 2A, 2B, and/or FIG. 3) according to an embodiment of the disclosure. FIG. 7 is a flow diagram illustrating an operation of calculating blood pressure change information according to sleep in an electronic device according to an embodiment of the disclosure.

Referring to FIG. 6, the processor (e.g., the processor 120 in FIG. 1 or FIG. 3) may extract feature points from blood pressure values calculated by analyzing the sensor value acquired through the optical sensor 310 for a specified time (e.g., 24 hours) and display the extracted feature points as a graph. For example, in FIG. 6, a line 601 connecting feature points of systolic blood pressure (SBP) among the calculated blood pressure values is represented along a time axis and a blood pressure level axis.

The SBP values in FIG. 6 may be determined, for example, based on a timing (or time interval) between peak values from a waveform of sensor signals (e.g., PPG signals) acquired through the optical sensor 310. For example, based on the timing (or time interval) between the peak values of the acquired sensor signals, the cardiac output (CO) and/or total peripheral resistance (TPR) may be extracted, and based on the extracted CO and/or TPR, the blood pressure (BP) may be estimated as, for example, "BP=CO×TPR". Here, the CO may refer to a blood flow ejected from the heart, and the TPR may indicate the degree of resistance of the blood vessels to the ejected blood flow.

According to an embodiment of the disclosure, the processor 120 may periodically acquire the sensor values through the optical sensor 310, sample a representative waveform by overlapping or filtering the acquired sensor values, and estimate the blood pressure based on the waveform. According to an embodiment of the disclosure, when estimating the blood pressure, the processor 120 may correct estimated blood pressure values based on, for example, user activity information and/or reference waveform information. In general, systolic blood pressure and diastolic blood pressure are associated with the nervous system and may be affected by user's respiration and movement levels and activation levels of associated sympathetic and parasympathetic nerves. Sleep is a stage in which the parasympathetic nervous system is activated, and it is common that there is little activity and the respiration is slowed, resulting in a drop in blood pressure. If the blood pressure does not drop despite the sleep state, it can be considered that a problem situation has occurred.

According to an embodiment of the disclosure, the processor 120 may continuously monitor the PPG values through the optical sensor 310 to estimate the blood pressure value, and the blood pressure value acquisition based thereon may be performed, for example, in units of 1 minute, 10 minutes, or 1 hour.

For example, by analyzing a change in the line 601 indicating the systolic blood pressure, it is possible to find out that there is a drop in blood pressure in a sleep interval 607. For example, for the sleep interval 607 determined based on the sensor values of the optical sensor 310 and/or the motion sensor (e.g., the motion sensor 320 in FIG. 3), it is possible to analyze a sleep state by using a blood pressure value or information on a change in blood pressure value estimated from the sensor value acquired by driving the optical sensor 310.

According to an embodiment of the disclosure, the sleep interval 607 may also be estimated using a line 602 indicating change information of the heart rate (HR). For example, in order to determine a sleep or not and/or analyze a sleep state, the processor 120 may use a heart rate variability (HRV) value. According to an embodiment of the disclosure, the processor 120 may determine the sleep interval by converting the sensor value (PPG signal) of the optical sensor 310 into a frequency domain, then performing filtering for each frequency range, and calculating a ratio (LF:HF) of the peak intensity of respective frequency ranges (e.g., a low frequency range of 0.04 to 0.15 Hz and a high frequency range of 0.15 to 0.4 Hz). For example, the sleep interval may include WBSO (wake before sleep onset), WASO (wake after sleep onset), S1 (sleep stage 1), S2 (sleep stage 2), SWS (slow wave sleep), and REMS (rapid eye movement sleep).

According to an embodiment of the disclosure, the processor 120 may determine the degree of blood pressure drop, based on a difference between an average systolic blood pressure value in the sleep interval 607 and an average systolic blood pressure value 603 in the daily activity state. For example, the degree of blood pressure drop may be determined by calculating the difference 605 between the average systolic blood pressure value 603 in the daily activity state (hereinafter referred to as a daily average blood pressure) and the average systolic blood pressure value 604 in the sleep state (hereinafter referred to as a sleep average blood pressure). In the example of FIG. 6, the degree of blood pressure drop is calculated to be approximately 10%, and thus it may be determined as a low blood pressure drop level. For example, by analyzing the line 601 connecting the feature points of blood pressure changes, it is possible to identify a blood pressure drop pattern in a hypnagogic interval 608 entering the sleep state and a blood pressure rise pattern in a hypnopompic interval 609 transitioning from the sleep state to the daily activity state.

Referring to FIG. 7, at operation 701, the processor (e.g., the processor 120 in FIG. 1 or FIG. 3) may determine a sleep or not, based on the sensor value measured through the optical sensor 310 and/or the motion sensor 320.

According to an embodiment of the disclosure, the processor 120 may determine whether the state is in a sleep state or not, by identifying the user state information based on the sensor value detected through the optical sensor 310 and/or the motion sensor 320 and thereby monitoring the user's current state.

According to various embodiments of the disclosure, when it is determined that the user's current state is a sleep state, the processor 120 may extract, at operation 703, blood pressure change feature points as shown in FIG. 6 by driving the optical sensor 310 to acquire the sensor value (e.g., the PPG value) and estimating the blood pressure from the acquired sensor value.

According to an embodiment of the disclosure, upon determining that the user is in the sleep state, the processor 120 may acquire the sensor value for estimating the blood pressure value by changing the driving method of the optical sensor 310 including the setting of driving timing, light intensity, and/or light wavelength as described above.

According to an embodiment of the disclosure, the processor 120 may estimate the blood pressure by extracting a pulse wave from the sensor value outputted through the optical sensor 310 and extracting feature points through a pulse wave analysis on the waveform of the pulse wave indicating a change according to cardiac output and blood vessel resistance. For example, the processor 120 may estimate the user's blood pressure by extracting a pulse wave period from a plurality of sensor values outputted through the optical sensor 310 and calculating a pulse wave velocity.

According to an embodiment of the disclosure, based on the calculated blood pressure value, the processor 120 may extract a blood pressure change feature point. For example, the blood pressure change feature point may include a blood pressure value drop or rise point. For example, the blood pressure change feature point may be a point at which the blood pressure value changes from drop to rise or from rise to drop. In the graph of FIG. 6, the blood pressure change feature points may be represented by, for example, vertices P constituting the bent line 601.

According to various embodiments of the disclosure, at operation 705, the processor 120 may analyze the sleep state based on the blood pressure change feature points. For example, by analyzing a change trend of the blood pressure change feature points as shown in FIG. 6, the processor 120 may determine whether a drop in blood pressure occurs in the sleep interval. For example, the processor 120 may analyze the change trend of the blood pressure change feature points and, if the average blood pressure value 604 in the sleep interval 607 is significantly lower than the average blood pressure value 603 in the daily activity state and if the low state is maintained for a specified time (e.g., 2 hours), may determine that a drop in blood pressure by sleep occurs. According to an embodiment of the disclosure, the processor 120 may perform blood pressure monitoring and sleep monitoring through the optical sensor 310 and, if the sleep state is identified by the sleep monitoring, may determine whether a drop in blood pressure occurs by driving the optical sensor 310 and detecting the blood pressure change feature points. According to an embodiment of the disclosure, when it is determined that a drop in blood pressure occurs, the processor 120 may determine through sleep monitoring whether the drop in blood pressure is caused by sleep.

According to various embodiments of the disclosure, the processor 120 may analyze a change in blood pressure according to sleep and thereby calculate blood pressure change information for determining a sleep state. For example, information calculated by analyzing the blood pressure change according to sleep may include, in addition to the presence or absence of blood pressure drop (dipper) according to sleep, the degree of the blood pressure drop (e.g., % level), a blood pressure change pattern in the sleep interval, a blood pressure drop pattern in the hypnagogic interval 608 entering the sleep state, and/or a blood pressure rise pattern in the hypnopompic interval 609 transitioning from sleep to daily life. For example, in the example of FIG. 6, it may be analyzed that the user has a drop in blood pressure according to sleep and the degree of the blood pressure drop is a low-level blood pressure drop of about 10%. For example, from the blood pressure change trend 601 in the sleep interval, it may be analyzed that the blood pressure value in the sleep interval is generally stable and a deep sleep is caught. Contrary to this, if a change in blood pressure value close to the daily average blood pressure occurs in the sleep interval, it may be determined that the person wakes up in the middle of sleep or does not catch a deep sleep. For example, the blood pressure drop pattern of the hypnagogic interval 608 may be analyzed as a pattern representing a relatively rapid blood pressure drop for about 1 hour, and the blood pressure rise pattern of the hypnopompic interval 609 may be analyzed as a pattern of repeating a partial drop and a partial rise for approximately 1 hour and 30 minutes and transitioning from a relatively gentle rise to a rapid rise.

Referring back to FIG. 5, at operation 540, the processor 120 may provide guide information according to the user's blood pressure change information.

According to various embodiments of the disclosure, the processor 120 may generate the guide information in response to the user's blood pressure change information. For example, the guide information may include information about a user's sleep quality or body rhythm, dietary or exercise-related information for improving the sleep quality or body rhythm, environment setting data including lighting or sound, music or meditation data, life guide information, and/or information, such as optimal alarm setting.

For example, the processor 120 may estimate a brain, heart, or kidney disease, based on the presence or absence of a drop in blood pressure and/or the degree of a drop in blood pressure (e.g., a low-level blood pressure drop (dipper), no blood pressure drop (non-dipper), a high-level blood pressure drop (extreme dipper), or a reverse-level blood pressure drop (reverse dipper)). For example, in case of the non-dipper or the reverse dipper, the processor 120 may determine it as a hypertensive group and, based on this, may provide the guide information regarding dietary control (e.g., limiting types and/or intakes of food, such as sodium, alcohol, or coffee) and/or exercise (e.g., prescribing various types of aerobic and/or anaerobic exercise and/or exercise duration).

For example, based on the blood pressure change pattern in the sleep interval, the blood pressure drop pattern in the hypnagogic interval 608 entering sleep, and/or the blood pressure rise pattern in the hypnopompic interval 609 transitioning from sleep to daily life, in case that a user's pattern is similar to a previous pattern, the processor 120 may not provide separate guide information in addition to the life guide information of a specified level.

For example, based on the blood pressure change pattern in the sleep interval, the blood pressure drop pattern in the hypnagogic interval 608 entering sleep, and/or the blood pressure rise pattern in the hypnopompic interval 609 transitioning from sleep to daily life, in case that a user's pattern is changed dramatically and/or the changed pattern is maintained for a specified date, the processor 120 may provide life guide information of an elevated level (e.g., hospital treatment recommendation).

For example, the processor 120 may estimate the sleep quality or body rhythm by analyzing the blood pressure change information according to sleep, such as the presence/absence of a blood pressure drop (dipper) interval according to sleep, a time length of the hypnopompic interval 609 transitioning from the dipper interval to a daily activity interval, and/or a blood pressure change pattern in the sleep interval.

According to various embodiments of the disclosure, the processor 120 may analyze the blood pressure change information according to sleep and, even in the sleep interval, may immediately provide a notification when an urgent event (e.g., excessive drop or rise in blood pressure during sleep) occurs.

According to various embodiments of the disclosure, the processor 120 may provide the guide information at a time point determined based on the blood pressure increase pattern out of the blood pressure drop interval. For example, the processor 120 may analyze the blood pressure change information according to sleep and provide the guide information at a time point of transitioning from the sleep interval to the hypnopompic interval 609, a time point of entering the daily activity state, or a time point after a specified time (e.g., after 1 hour).

According to various embodiments of the disclosure, the processor 120 may provide the guide information in the form of a screen including text or images, audio including voice or sound, and/or vibration through a display module (e.g., the display module 160 in FIG. 1 or FIG. 3), a sound output module (e.g., the sound output module 155 in FIG. 1), and/or a haptic module (e.g., the haptic module 179 in FIG. 1).

According to various embodiments of the disclosure, the processor 120 may transmit the above-described guide information to an external electronic device (e.g., the external electronic device 102 or 104 in FIG. 1 or the second electronic device 402 in FIG. 4) (e.g., a smartphone) to output the guide information through the external electronic device.

According to various embodiments of the disclosure, the processor 120 may receive feedback on the quality and/or condition of sleep from the user through an input module (e.g., the input module 150 in FIG. 1). For example, the processor 120 may analyze a correlation between the quality and/or condition of sleep and the blood pressure drop pattern through the user's feedback and provide the guide information based thereon. For example, when a sleep blood pressure drop pattern for a normal 7 hours is analyzed through the blood pressure change information analysis for the user and a feedback is received from the user that the quality of sleep is good, the processor 120 may provide a guide to light exercise according to a user's usual lifestyle, information to adjust a user's usual bedroom environment (e.g., temperature and/or illuminance), and/or guide information to set the optimal alarm time for a user's usual wake-up time in order to maintain the blood pressure drop pattern. For example, if a pattern different from the normal sleep blood pressure drop pattern appears, the processor 120 may additionally provide, as the guide information, music or meditation data for user's brain relaxation in addition to providing the light exercise guide according to the usual lifestyle, the information to adjust the user's usual bedroom environment (e.g., temperature and/or illuminance), and/or the guide information to set the optimal alarm time for the usual wake-up time.

While the disclosure has been shown and described with reference to various embodiments thereof, it will be understood by those skilled in the art that various changes in form and details may be made therein without departing from the spirit and scope of the disclosure as defined by the appended claims and their equivalents.

The invention claimed is:
1. An electronic device comprising:
a motion sensor;
at least one optical sensor;
memory storing one or more computer programs; and one or more processors communicatively coupled to the motion sensor, the at least one optical sensor, and the memory, wherein the one or more computer programs include computer-executable instructions that, when executed by the one or more processors individually or collectively, cause the electronic device to:

monitor user state information determined based on signals received through the motion sensor and the at least one optical sensor, identify, from the user state information, whether a user is in a daily activity state or a sleep state, acquire a sensor value by controlling the at least one optical sensor based on the user being identified as being in the sleep state, calculate blood pressure change during sleep of the user based on the sensor value, identify an information of the sleep state by analyzing the blood pressure change, and provide guide information according to the information of the sleep state, the guide information being provided at a time point based on identifying, from the information of the sleep state, the user transitioning out of the sleep state.

2. The electronic device of claim 1, wherein the one or more computer programs further include computer-executable instructions that, when executed by the one or more processors individually or collectively, cause the electronic device to:

drive the at least one optical sensor by adjusting at least one of a driving timing, an output light intensity, or an output light wavelength, based on the user state information.

3. The electronic device of claim 1, wherein the one or more computer programs further include computer-executable instructions that, when executed by the one or more processors individually or collectively, cause the electronic device to:

calculate blood pressure values based on sensor values acquired from the at least one optical sensor for a specified time, and calculate the blood pressure change by extracting feature points from the blood pressure values.

4. The electronic device of claim 3, wherein the one or more computer programs further include computer-executable instructions that, when executed by the one or more processors individually or collectively, cause the electronic device to:

analyze the feature points of the blood pressure change, and thereby identify the information of the sleep state including at least one of a presence or absence of a blood pressure drop according to sleep, a degree of the blood pressure drop, a pattern of a blood pressure drop interval, a blood pressure drop pattern entering the blood pressure drop interval, or a blood pressure rise pattern leaving the blood pressure drop interval.

5. The electronic device of claim 4, wherein the one or more computer programs further include computer-executable instructions that, when executed by the one or more processors individually or collectively, cause the electronic device to:

determine the guide information to be provided to the user, based on the information of the sleep state, and provide the guide information at a time point determined based on the blood pressure rise pattern leaving the blood pressure drop interval.

6. The electronic device of claim 4, wherein the one or more computer programs further include computer-executable instructions that, when executed by the one or more processors individually or collectively, cause the electronic device to:

analyze a change trend of the feature points, and extract, as the blood pressure drop interval according to sleep, an interval maintained for a specified period after the blood pressure is relatively low.

7. The electronic device of claim 6, wherein the one or more computer programs further include computer-executable instructions that, when executed by the one or more processors individually or collectively, cause the electronic device to:

calculate the degree of the blood pressure drop according to sleep by comparing an average blood pressure value of the blood pressure drop interval with an average blood pressure value of an interval other than the blood pressure drop interval.

8. The electronic device of claim 1, wherein the one or more computer programs further include computer-executable instructions that, when executed by the one or more processors individually or collectively, cause the electronic device to:

provide the guide information in a form of at least one of a screen including text or images, audio including voice or sound, or vibration.

9. The electronic device of claim 1, wherein the one or more computer programs further include computer-executable instructions that, when executed by the one or more processors individually or collectively, cause the electronic device to:

monitor the user state information by acquiring at least one of a heart rate (HR) or a heart rate variation (HRV) from the signal received through the at least one optical sensor.

10. The electronic device of claim 9, wherein the one or more computer programs further include computer-executable instructions that, when executed by the one or more processors individually or collectively, cause the electronic device to:

monitor the user state information by analyzing at least one of a magnitude or a frequency of the signal received through the motion sensor.

11. The electronic device of claim 1, wherein the information of the sleep state includes information of at least one of a quality or a condition of sleep.

12. The electronic device of claim 1, wherein the one or more computer programs further include computer-executable instructions that, when executed by the one or more processors individually or collectively, cause the electronic device to:

based on the user being identified as being in the sleep state, identify, from the monitored user state information, whether the user is in a shallow sleep stage or a deep sleep stage, and acquire the sensor value by controlling the at least one optical sensor based on the user being identified as being in the deep sleep stage.

13. A method performed by an electronic device including a motion sensor and at least one optical sensor, the method comprising:

monitoring user state information determined based on signals received through the motion sensor and the at least one optical sensor;

identifying, from the user state information, whether a user is in a daily activity state or a sleep state;

acquiring a sensor value by controlling the at least one optical sensor based on the user being identified as being in the sleep state;

calculating blood pressure change during sleep of the user based on the sensor value;

identifying an information of the sleep state based on the blood pressure change; and providing guide information according to the information of the sleep state, the guide information being provided at a time point based on identifying, from the information of the sleep state, the user transitioning out of the sleep state.

14. The method of claim 13, wherein the acquiring of the sensor value includes driving the at least one optical sensor by adjusting at least one of a driving timing, an output light intensity, or an output light wavelength, based on the user state information.

15. The method of claim 13, wherein the calculating of the blood pressure change includes:

calculating blood pressure values based on sensor values acquired from the at least one optical sensor for a specified time, and calculating the blood pressure change by extracting feature points from the blood pressure values.

16. The method of claim 15, wherein the calculating of the blood pressure change includes:

analyzing the feature points of the blood pressure change, and thereby identifying the information of the sleep state including at least one of a presence or absence of a blood pressure drop according to sleep, a degree of the blood pressure drop, a pattern of a blood pressure drop interval, a blood pressure drop pattern entering the blood pressure drop interval, or a blood pressure rise pattern leaving the blood pressure drop interval.

17. The method of claim 16, wherein the providing of the guide information includes:

determining the guide information to be provided to the user, based on the information of the sleep state; and providing the guide information at a time point determined based on the blood pressure rise pattern leaving the blood pressure drop interval.

18. The method of claim 17, wherein the providing of the guide information includes providing the guide information in a form of at least one of a screen including text or images, audio including voice or sound, or vibration.

19. The method of claim 17, wherein the calculating of the blood pressure change includes:

analyzing a change trend of the feature points, and extracting, as the blood pressure drop interval according to sleep, an interval maintained for a specified period after the blood pressure is relatively low.

20. The method of claim 19, wherein the calculating of the blood pressure change includes calculating the degree of the blood pressure drop according to sleep by comparing an average blood pressure value of the blood pressure drop interval with an average blood pressure value of an interval other than the blood pressure drop interval.

21. The method of claim 13, wherein the monitoring of the user state information includes monitoring the user state information by acquiring at least one of a heart rate (HR) or a heart rate variation (HRV) from the signal received through the at least one optical sensor.

22. The method of claim 21, wherein the monitoring of the user state information includes monitoring the user state information by analyzing at least one of a magnitude or a frequency of the signal received through the motion sensor.

23. One or more non-transitory computer-readable storage media storing one or more computer programs including computer-executable instructions that, when executed by one or more processors of an electronic device individually or collectively, cause the electronic device to perform operations, the operations comprising:

monitoring user state information determined based on signals received through a motion sensor and at least one optical sensor;

identifying, from the user state information, whether a user is in a daily activity state or a sleep state;

acquiring a sensor value by controlling the at least one optical sensor based on the user being identified as being in the sleep state;

calculating blood pressure change during sleep of the user based on the sensor value;

identifying an information of the sleep state based on the blood pressure change; and providing guide information according to the information of the sleep state, the guide information being provided at a time point based on identifying, from the information of the sleep state, the user transitioning out of the sleep state.

* * * * *